(12) United States Patent
Buzatu et al.

(10) Patent No.: US 7,608,240 B2
(45) Date of Patent: *Oct. 27, 2009

(54) NANOTUBES FOR CANCER THERAPY AND DIAGNOSTICS

(75) Inventors: Dan A. Buzatu, Benton, AR (US); Jon G. Wilkes, Jefferson, AR (US); Dwight Miller, Jefferson, AR (US); Jerry A. Darsey, Little Rock, AR (US); Tom Heinze, Jefferson, AR (US); Alex Biris, Little Rock, AR (US); Richard Berger, White Hall, AR (US); Mark Diggs, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 851 days.

This patent is subject to a terminal disclaimer.

(21) Appl. No.: 11/005,380

(22) Filed: Dec. 6, 2004

(65) Prior Publication Data

US 2006/0067939 A1 Mar. 30, 2006

Related U.S. Application Data

(60) Provisional application No. 60/527,454, filed on Dec. 5, 2003, provisional application No. 60/553,907, filed on Mar. 17, 2004.

(51) Int. Cl.
*A61K 51/00* (2006.01)
*A61M 36/14* (2006.01)
(52) U.S. Cl. .............. 424/1.49; 424/1.11; 424/1.81; 424/1.29; 530/387.1
(58) Field of Classification Search ............ 424/1.11, 424/1.21, 1.29, 1.37, 1.49, 1.65, 9.1, 9.3, 424/9.4, 9.5, 9.6, 9.7, 9.8, 1.89, 489, 178.1; 530/387.1
See application file for complete search history.

(56) References Cited

U.S. PATENT DOCUMENTS 5,565,215 A * 10/1996 Gref et al. ............... 424/501

6,165,440 A * 12/2000 Esenaliev ............... 424/1.11

OTHER PUBLICATIONS

Hawthorne et al., "A critical assessment of boron target compounds for boron neutron capture therapy" 62 J. Neuro-Oncology (2003), pp. 33-45.
Chopra et al., "Measurement of the elastic modulus of a multi-wall boron nitride nanotube" 105 Solid State Commun. (1998), pp. 297-300.
Cumings et al., "Mass-production of boron nitride double-wall nanotubes and nanococoons", 316 Chem. Phys. Lett. (2000), pp. 211-216.
Demczyk et al., "Structure of boron nitride nanotubules", 78 Appl. Phys. Lett. 18 (2001), pp. 2772-2774.
Mickelson et al., "Packing C60 in boron nitride nanotubes", 300 Science, (2003), pp. 467-469.
Bahr et al., "Covalent chemistry of single-wall carbon nanotubes" 12 J. Mater. Chem. (2002), pp. 1952-1958.
Immobilized Affinity Ligand Techniques, Hermanson et al., Eds., Academic Press, New York (1992), p. 45.
Liu et al., "Fullurene pipes", 280 Science (1998), pp. 1253-1256.
Korfmacher et al., "Analysis of 1- and 4-nitropyrene and 1-nitopyrene-d9 via fused siloca . . . ", 7 J. High Resolut. Chrom. Commun. (1984), pp. 581-583.
Miller et al., "Synthesis of nitropolycyclic aromatic hydrocarbons with the substituent at the longest axis", 57 J. Org. Chem. (1992), pp. 3746-3748.
Ledingham et al., "Laser-driven photo-transmutation of 129I—a long-lived nuclear waste product" 36 J. Phys. D: Appl. Phys. (2003), pp. L79-L82.
Zhang, et al., "Rapid ring-opening polymerization of D,L-Lactide by microwaves", 25 Macromol. Rapid Commun. (2004), pp. 1402-1405.
Yanch et al., "Boron neutron capture synovectomy: Treatment of rheumatoid arthritis . . . ", 26 Med. Phys. 3 (1999), pp. 364-375.

* cited by examiner

*Primary Examiner*—Dameron L Jones
(74) *Attorney, Agent, or Firm*—Winstead PC

(57) ABSTRACT

The present invention provides a novel approach to cancer therapy and diagnostics that utilizes nanotubes and other similar nanostructures as both an indirect source of radiation therapy (BNCT), and as delivery vehicles for other types of radio- and chemo-therapeutic materials, as well as imaging agents for diagnostic purposes.

13 Claims, 3 Drawing Sheets

NANOTUBES FOR CANCER THERAPY AND DIAGNOSTICS

CROSS-REFERENCE TO RELATED APPLICATIONS

This Application claims priority to U.S. Provisional Patent Application Ser. Nos. 60/527,454, filed Dec. 5, 2003; and 60/553,907, filed Mar. 17, 2004.

FEDERALLY SPONSORED RESEARCH

The present invention was made with support from the United States Food and Drug Administration.

FIELD OF THE INVENTION

The present invention relates generally to cancer therapy methods, and more specifically to the use of novel nanostructure-antibody species as delivery vehicles for such therapies.

BACKGROUND OF INVENTION

Radiation therapy (radiotherapy) is well-established in the treatment of cancers. Such radiation generally involves the localized delivery of radiation to the site of a tumor, wherein such radiation is generally in the form of X-rays, beta particles ($\beta^-$, i.e., electrons), gamma radiation ($\gamma$), and/or alpha particles ($\alpha$, i.e., helium nuclei). Such radiation therapy relies on the free radical disruption of cellular DNA to destroy cancer cells in a targeted manner. Radiation may come from a machine outside the body (external-beam radiation therapy), or it may come from radioactive material placed in the body near cancer cells (internal radiation therapy, implant radiation, or brachytherapy). Systemic radiation therapy uses a radioactive substance, such as a radiolabeled monoclonal antibody, that circulates throughout the body. Such internal radiation therapy (localized or systemic) typically involves a careful selection of material comprising radioactive isotopes (radioisotopes) capable of delivering the desired type and amount of radiation.

Radioisotopes also find use as medical diagnostic tools. An example of this is in positron emission tomography (PET), wherein radioisotopes capable of emitting positrons ($\beta^+$) find application. Other radioisotope-based diagnostic tools include gamma cameras and single photon emission computer tomography (SPECT). With the increasing use of radiopharmaceuticals with specific biological affinities, gamma cameras and SPECT have become increasingly important diagnostic tools. These tools have been used to image virtually every organ in the body. Brain tumors, for example, can be located by SPECT after intravenous injection of $Na^{99m}TcO_4$, as brain tumors have a very high affinity for Tc. Alzheimers disease has been studied using a gamma camera and the radioisotope $^{133}Xe$. Other radioisotopes and their medical uses include $^{133}Xe/^{99m}Tc$ for pulmonary embolism, $^{123}I/^{99m}Tc$ for renal function, and $^{201}Tl$ for cardiac infarction and ischaemia.

Boron Neutron-Capture Therapy

Boron Neutron Capture Therapy (BNCT) is an experimental approach to cancer treatment that is based on a dual-step technique: accumulation of a boron-containing compound within a tumor and treatment with a beam of low-energy neutrons directed at the boron-containing tumor. The nuclei of the boron atoms capture the neutrons and split into two highly charged particles (alpha particle and lithium ion) that have very short path lengths, approximating one cell diameter. These charged particles release sufficient energy locally to kill any tumor cells that contain high concentrations of boron. Over the past nine years, the United States Dept. of Energy (DOE) has supported a nationwide research program to develop BNCT for clinical use.

Catching Neutrons to Combat Cancer

Subjecting boron atoms to low-energy neutron radiation (thermal neutrons) causes the boron nuclei to disintegrate into alpha particles and lithium isotopes with a kinetic energy of 2.5 MeV. When this disintegration occurs in malignant cells, the energy generated is sufficient to destroy them without damaging the neighboring cells, since the range of the particles is only about 10 microns. In such BNCT, it has been estimated that it takes $10^9$ boron atoms per tumor cell for a therapeutic dose. See Hawthorne et al., J. Neuro-Oncology, (2003) 62: 33-45. As each tumor cell has about 106 effective antigenic sites that can act as targets, the number of boron atoms required per carrier has been calculated to be $10^3$. Thus, 1,000 boron atoms are needed per antibody molecule for effective treatment. However, this has been heretofore impractical because when this many small carbo-borane molecules are attached to the antibody molecule, it loses its tumor-specific targeting ability. Hawthorne et al.

Other boron-containing compounds (e.g., porphyrins containing boron) currently being used in such therapies, however, generally comprise only a very small amount of boron. It would be useful if a molecular species with a higher percentage of boron (wt. % relative to the overall molecular weight of the molecule) could be used in BNCT.

Boron Nitride Nanotubes

Boron nitride (BN) nanotubes have been synthesized and shown to behave in many ways like their carbon nanotube analogues [Chopra et al., Solid State Commun., (1998) 105: 297-300; Cumings et al., Chem. Phys. Lett., (2000) 316: 211-216]. For example, they show the same propensity to agglomerate into bundles held together by van der Waals attractive forces. Furthermore, they have been observed to exist as single- or multi-walled varieties. There are notable differences, however, namely that they are insulating and possess a constant bandgap of 5 eV irrespective of tube diameter, number of walls, and chirality [Demczyk et al., Appl. Phys. Lett., (2001) 78(18): 2772-2774; Mickelson et al., Science, (2003) 300: 467-469].

Use of such BN nanotubes (BNnt), such as those described above, in BNCT would be very advantageous on a percent boron basis—if BN nanotubes could be made therapeutically deliverable. Additionally, other types of nanotubes and nanostructures could be made to serve as delivery vehicles in cancer treatments and in diagnostic imaging. A related advantage is the ability to attach BN nanostructures to an IgG or other targeting biomolecule at only one or a few locations, so that the attached therapeutic atoms do not cover or interfere with the target molecule's receptor and thus compromise specificity.

BRIEF DESCRIPTION OF THE INVENTION

The present invention is directed to novel methods and compositions for the treatment of cancer, wherein such methods and compositions utilize nanotubes and other similar nanostructures as both an indirect source of radiation therapy, and as delivery vehicles for other types of radio- and chemotherapeutic materials, as well as imaging agents for diagnostic purposes.

Some embodiments of the present invention involve the use of BN nanostructures in boron neutron capture therapy (BNCT). In some embodiments, antibody species are attached to the BN nanostructures to enable them to target tumors when administered to a mammalian subject. These tumor-targeting species are referred to herein as BN nanostructure-antibody composite species. Once such composite species are in the proximity of a tumor, they can be activated with transdermal neutrons. Once activated, the $^{10}$B atoms emit alpha particles that are capable of destroying cancerous cells.

In some embodiments of the present invention, carbon nanostructures (e.g., carbon nanotubes) are used to deliver radiation to a target region. In such embodiments, radioactive isotopes, such as $^{128}$I, are attached to a carbon nanostructure to which one or more antibody species are attached. These radioactive-laden carbon nanotube-antibody species can then be employed to selectively target tumors when administered to a mammalian subject.

In other embodiments, tumor cloned IgGs are used to carry nanocontainers (e.g., single-wall carbon nanotubes), bound to the IgGs, to the tumor sites. Ultrasonic waves are then used to explode the carbon nanotubes in the proximity of the tumor. Ultrasound is capable of penetrating deep through tissue without tissue damage because the frequency of the waves can be adjusted to be absorbed only by the target, here carbon or other nanostructures. The technique can also be used to deliver effective chemotherapeutic substances, toxic to a tumor, encapsulated inside the nanostructures.

In all of the above-mentioned embodiments, the BN nanostructures, the carbon nanostructures, and the nanocontainers (nanovessels), can all be encapsulated with a bio-polymer. In some of these embodiments, the antibody species is attached to the nanostructure/nanocontainer through the bio-polymer. Encapsulating materials such as these with bio-polymers can circumvent the need to attach the antibody species (e.g., IgG), and it can reduce potential nanoparticle toxicity and/or enhance the solubility of the IgG-nanostructure complexes in biological fluids.

The foregoing has outlined rather broadly the features of the present invention in order that the detailed description of the invention that follows may be better understood. Additional features and advantages of the invention will be described hereinafter which form the subject of the claims of the invention.

DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
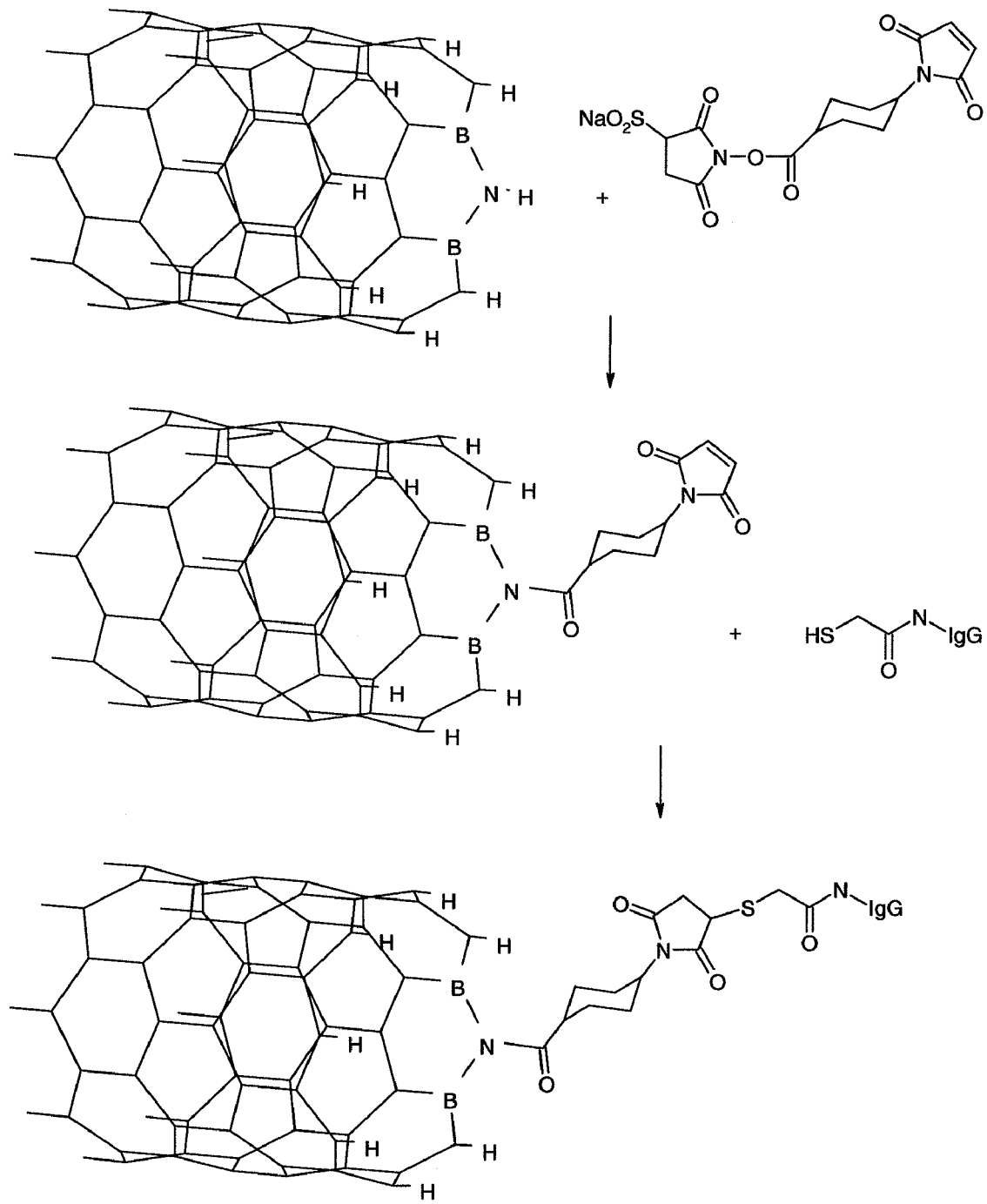
FIG. 1 illustrates, schematically, the attachment of IgG to a BN nanotube via a covalent linkage, in accordance with some embodiments of the present invention.

The present invention provides a novel approach to cancer therapy and diagnostics that utilizes nanotubes and other similar nanostructures as both an indirect source of radiation therapy (BNCT), and as delivery vehicles for other types of radio- and chemo-therapeutic materials, as well as imaging agents for diagnostic purposes.

In some embodiments of the present invention, boronnitride (BN) nanostructures are used, particularly for BNCT. BN nanostructures, according to the present invention, include, but are not limited to, BN nanotubes, BN nanoscrolls, BN nanofibrils, BN nanovessels, BN nanocontainers, and combinations thereof. In the discussions which follow, an exemplary BN nanostructure, a BN nanotube (BNnt), will be used when describing various embodiments of the present invention. It should, however, be understood by those of skill in the art that other BN nanostructures could be utilized without departing from the spirit and scope of the present invention. In addition, BCN nanostructures (nanostructures in which a portion of the carbon atoms have been replaced by boron and nitrogen atoms) are types of BN nanostructures, which can also be used within the scope of the present invention.

BN nanotubes, according to the present invention, may comprise a variety of diameters, tube lengths, and chiralities. They may comprise one or more "walls" in their structural composition, although studies have suggested that there is a stabilizing effect for BN nanotubes comprising two walls. Further, they may be either open ended or capped, and they may be chemically functionalized on their ends, sidewalls, or both.

In some embodiments of the present invention, carbon nanostructures are employed. In the discussions which follow, an exemplary carbon nanostructure, a carbon nanotube (CNT), will be generally used when describing various embodiments of the present invention. It should, however, be understood by those of skill in the art that other carbon nanostuctures could be utilized without departing from the spirit and scope of the present invention.

Carbon nanotubes, according to the present invention, include, but are not limited to, single-wall carbon nanotubes, multi-wall carbon nanotubes, double-wall carbon nanotubes, buckytubes, fullerene tubes, carbon fibrils, carbon nanotubules, carbon nanofibers, vapor-grown carbon fibers, and combination thereof. They may comprise a variety of lengths, diameters, chiralities, number of walls, and they may be either open or capped at their ends. Furthermore, they may be chemically functionalized in a variety of manners, some of which are described in Bahr et al., J. Mater. Chem., (2002) 12: 1952-1958, incorporated by reference herein.

Other nanostuctures, according to the present invention, comprise nanospheres, nanoshells, nested nanoshells, nanovessels, fullerenes, nested fullerenes, nanowires, nanorods, nanococoons, and combinations thereof.

In some embodiments of the present invention, tumorcloned antibodies are employed. In the discussions which follow, exemplary tumor-cloned antibodies, immunoglobulins (IgGs), will be generally used when describing various embodiments of the present invention. It should, however, be understood by those of skill in the art that other suitable antibodies could be utilized without departing from the spirit and scope of the present invention.

Use of Boron Nitride Nanotubes

Some embodiments of the present invention are directed to variations of boron neutron capture therapy (BNCT) using radio-activated boron-nitride (BN) nanotubes attached to tumor-cloned immunoglobulins (IgGs), to deliver intense, short-lived, therapeutic doses of radiation specifically to active tumor sites or disbused metastatic cells. A nanotube and IgG are attached if they remain associated with one another such that the therapeutic dose is delivered to the targeted active tumor sites. In some embodiments, this attachment is a covalent-type bonding, and the resulting molecular composite termed a BN nanotube-immunoglobulin (BNnt-IgGs) species.

BNCT is a technique that relies on (non-radioactive) $^{10}B$ being delivered specifically to a tumor site, and then activating it using an accurate beam of epithermal neutrons, which are low energy neutrons with velocities adjusted to penetrate tissue to the specific tumor depth, where the $^{10}B$ has lodged.

A BN nanotube's structure is similar to the "rolled-up-graphite" structure of a carbon nanotube; six-membered rings, but with boron atoms being singly bound to 3 surrounding nitrogen atoms, and the nitrogen atoms bound to surrounding boron atoms (no conjugation). Thus, each BN nanotube is composed of a substantial number of boron atoms, i.e., 50%, meaning hundreds to thousands for each nanotube.

Boron has a relatively large radioactive cross section and so can be easily made radioactive in a neutron flux. Radioactive boron is an alpha and gamma emitter with isotopes of $^{12}B$ and $^{13}B$, having γ energies of 4.439 MeV and 3.68 MeV, respectively. The alpha particles may or may not have enough energy to kill cells unless the nanotubes actually penetrate the cell walls through the unattached ends. The gamma rays should do enough damage for therapy, especially since there will be many generated from the multitude of boron atoms associated with the BN nanotubes. There will also be a local toxic effect from a lithium ion produced as each radioactive boron atom decays. In an aqueous environment, $Li^+$ should produce LiOH, a very strong base, which can do a lot of damage to cancer cells, but is likely to be rapidly diluted in any aqueous body fluids or media (cellular fluids as well as plasma). Thus, using the BNnt-IgGs species in BNCT, it is possible to deliver a highly concentrated dose of radiation precursor (boron) to intended targets (tumors or individual cancer cells) with great specificity.

Referring to FIG. 1, in some embodiments of the present invention, covalent attachment of the BN nanotubes to the IgG relies on the terminal nitrogen atoms of each tube, themselves terminated with hydrogen, and can be accomplished using a linker reaction described previously for linking antibodies to surfaces through secondary amine linkages [Immobilized Affinity Ligand Techniques, Hermanson et al., Eds., Academic Press, New York: 1992, p. 45, incorporated herein by reference], wherein BN nanotube 1 is reacted with Sulfo-succinimidyl 4-[N-maleimidomethyl]cyclohexane-1-carboxylate (Sulfo-SMCC) 2 to yield intermediate product 3, which in turn is reacted with sulfhydral functionalized IgG 4 to yield BN nanotube-IgG composite species 5.

The chemistry illustrated in FIG. 1 is not the only type of linker chemistry, only an example. Such linker chemistry can be optimized with respect to the inherent reactivity of the BN nanotube terminal NH moiety. While not intending to be bound by theory, the reactivity of the nanotube terminal NH group is believed to be similar to a normal small molecule NH group. If the BN nanotube diameter is too small, ring strain may exist in the BN structure. In this situation attachment of the Sulfo-SMCC molecule to form intermediate product 3 may create small aberrations in the ring structure, lead to tube fracture, and possibly even substitution in the internal portions of the ring-system. It is envisioned that, in some embodiments, more than one BN nanotube is attached to an IgG molecule. In other embodiments, multiple IgG molecules are attached to a single BN nanotube. In some embodiments, there may be multiple linkers between the BN nanotube and the IgG.

In some embodiments, there may be issues that have to be overcome to get BN nanotubes into solution. These issues may be solved (at least in part) by reducing the size (width and length) of the BN nanotubes. In some embodiments, solubility issues can be overcome via chemical functionalization and/or other modification of the BN nanotubes. For example, it may also be possible to put propylene glycol or other polar groups on the BN nanotube ends to improve BN nanotube solvation. In some embodiments, surfactants may be employed to facilitate solubility.

The therapy will involve activation of the BN nanotubes with a neutron beam (as in BNCT) once the IgG carrier molecules have reached their target tissue. This invention addresses three limitations in the present art of BNCT: (1) specificity, meaning the ability to target accurately the tumor tissue, (2) the amount of radiation, that is, how many boron atoms can be delivered to the tumor site, and (3) non-applicability for metastasized cells, resolvable by this invention because the vast number of boron atoms per nanotube can accelerate achievement of a local therapeutic dose and allow meaningful large area (even whole body) neutron activation strategies. Most molecules that are currently used by BNCT can only deliver one or two boron atoms per molecule and do so without the cancer cell target specificity associated with an IgG. Thus, BNCT is only as specific as the columnation of the neutron-activating beam allows. The present invention, using BN nanotubes can deliver significant numbers of boron atoms (100s to 1000s) specifically to the tumor site while avoiding exposures to surrounding tissue.

Methods of activating BN nanotubes with a neutron beam, in accordance with embodiments of the present invention pertaining to BNCT, include, but are not limited to, neutron activation. Neutron activation is a process where a material placed in a neutron flux absorbs neutrons in proportion to its neutron activation cross section. The thermal neutron activation cross section ($\sigma_a$) is a number experimentally measured, which is proportional to how "sensitive" an atom is to absorbing neutrons. The unit of measurement, called a Barn, is equal to $10^{-28}$ $m^2$. When an atom absorbs a neutron, it will be transformed to an isotope of the same element, but one atomic mass unit higher. This usually results in the new isotope being radioactive. Common reactions observed with neutron activation are (n,γ), (n,p), and (n,α). This notation indicates that a neutron is being absorbed by a particular nuclei and a gamma ray, proton or alpha particle is being expelled, respectively. The BNCT described herein involves $^{10}B$, which is given by $^{10}B(n,\alpha)^7Li$, where $^{10}B$ ($\sigma_a$=3838 Barns) is being activated by a neutro and an alpha (α) particle is ejected with the result that a $^7Li$ is produced. This is the most common reaction with the isotope $^{10}B$, and it is practically instantaneous.

Furthermore, by using BNnt attached to IgGs (such as BNnt-IgGs species), this allows for whole body BNCT treatment in which the whole body being treated can be radioactivated with a diffuse epithermal neutron beam. Through the use of the IgGs, the disclosed BNnt-based therapy confers cell-level specificity. The boron atom load of the BNnt is sufficiently concentrated that effective dosing is possible with a much shorter activation time in any one region of the body. Such a process can be used in combination with more aggressive activation on specific target sites. For instance, identified tumors can first be targeted with one level of activation, followed by a lighter dose of neutrons for remaining parts of the body.

While the embodiments described above have been directed primarily at targeting identified tumor cell with a high degree of specificity, diffuse neutron beams can be employed in volumes around the periphery of tumor masses, along lymph ducts and in the glands, and even in whole-body irradiation therapies. Such embodiments would allow for the destruction even of metastasized cells.

Use of Carbon Nanostructures

In some embodiments of this invention, tumor cloned IgGs (or other suitable antibodies) are utilized to carry carbon nanostructures (e.g.—carbon nanotubes) that are attached to the IgGs, and that carry a substantial amount of radioactive material specifically to tumor sites. Such nanostructure-IgG composites comprising a radioactive material are termed radioactive nanostructure-IgG species. When the nanostructure is a carbon nanotube, the radioactive nanostructure-IgG species is termed a radioactive CNT-IgG species. In some embodiments, the carbon nanotube (CNT) attachment to the IgG comprises covalent bonding, as described above for BN nanotubes, using known linker chemistry for CNTs. See Liu et al., Science, (1998) 280: 1253-1256, incorporated herein by reference.

The radioactive material carried by the nanostructure can be atomic or molecular in nature, and can be attached to the nanostructure before or after the nanostructure is attached to the IgG. Generally, this radioactive material can be any radioactive isotope or isotopes currently used in the medical treatment of cancer. In some embodiments, this radioactive material is an iodine isotope. Such an isotope can be present as a salt (e.g., $PbI_2$). An exemplary iodine isotope is $^{128}I$, which has a half-life of 25 minutes ($t_{1/2}$=25 min). Furthermore, since the IgGs carry the radioactive species before they reach the tumor site, in some embodiments, the IgGs can also hunt down metastasized cells in the body as they are recognized. This is similar in concept to the above-described BNCT embodiments, except that instead of activating the radioactive species at the tumor site, the species will be radioactive before the IgGs are introduced into the body. This is feasible because the $^{128}I$ has a 25-minute half-life whereas the radioactive boron nuclei (generated in situ) have microsecond half-lives. Other radioactive species could be used besides $^{128}I$. Other suitable radionuclei that can be employed depending upon the type of radiation desired, the intensity, and the duration (controlled by the half-life) include, but are not limited to, $^{121}I$ ($t_{1/2}$=2.12 hours), $^{124}I$ ($t_{1/2}$=4.17 days), $^{131}I$ ($t_{1/2}$=8.0days), $^{133}I$ ($t_{1/2}$=20.8 hours), $^{135}I$ ($t_{1/2}$=6.58 hours), isotopes of Tellurium, and combinations thereof. Essentially, any therapeutically-suitable radioisotope which can be attached to a nanostructure, which in turn can be attached to an IgG, can be used (CNT-antibody linker chemistry is well established in the scientific literature). Examples of radioactive isotopes commonly used in medical applications are shown in Table 1.

TABLE 1

| Isotope | Radiation type | Half-life ($t_{1/2}$) | Source (typical) | Use (typical) |
| --- | --- | --- | --- | --- |
| $^{99}Mo$ | $\beta^-$ | 65.94 hours | Nuclear reactor | Parent of $^{99m}Tc$ |
| $^{99m}Tc$ | Isomeric transition, $\gamma$ | 6.01 hours | Nuclear reactor | Diagnostic |
| $^{60}Cr$ | $\beta^-$ | 0.6 sec | Nuclear reactor | Diagnostic |
| $^{192}Ir$ | $\beta^-$ | 73.83 days | Nuclear reactor | Therapeutic |
| $^{32}P$ | $\beta^-$ | 14.28 days | Nuclear reactor | Therapeutic |
| $^{89}Sr$ | $\beta^-$ | 50.52 days | Nuclear reactor | Therapeutic |
| $^{90}Y$ | $\beta^-$ | 64.0 hours | Nuclear reactor | Therapeutic |
| $^{153}Sm$ | $\beta^-$ | 46.7 hours | Nuclear reactor | Therapeutic |
| $^{67}Ga$ | Orbital electron capture, $\gamma$ | 78.25 hours | Cyclotron | Diagnostic |
| $^{201}Tl$ | Orbital electron capture, $\gamma$ | 3.05 days | Cyclotron | Diagnostic |
| $^{123}I$ | Orbital electron capture, $\gamma$ | 13.1 hours | Cyclotron | Diagnostic |

Figure 2:
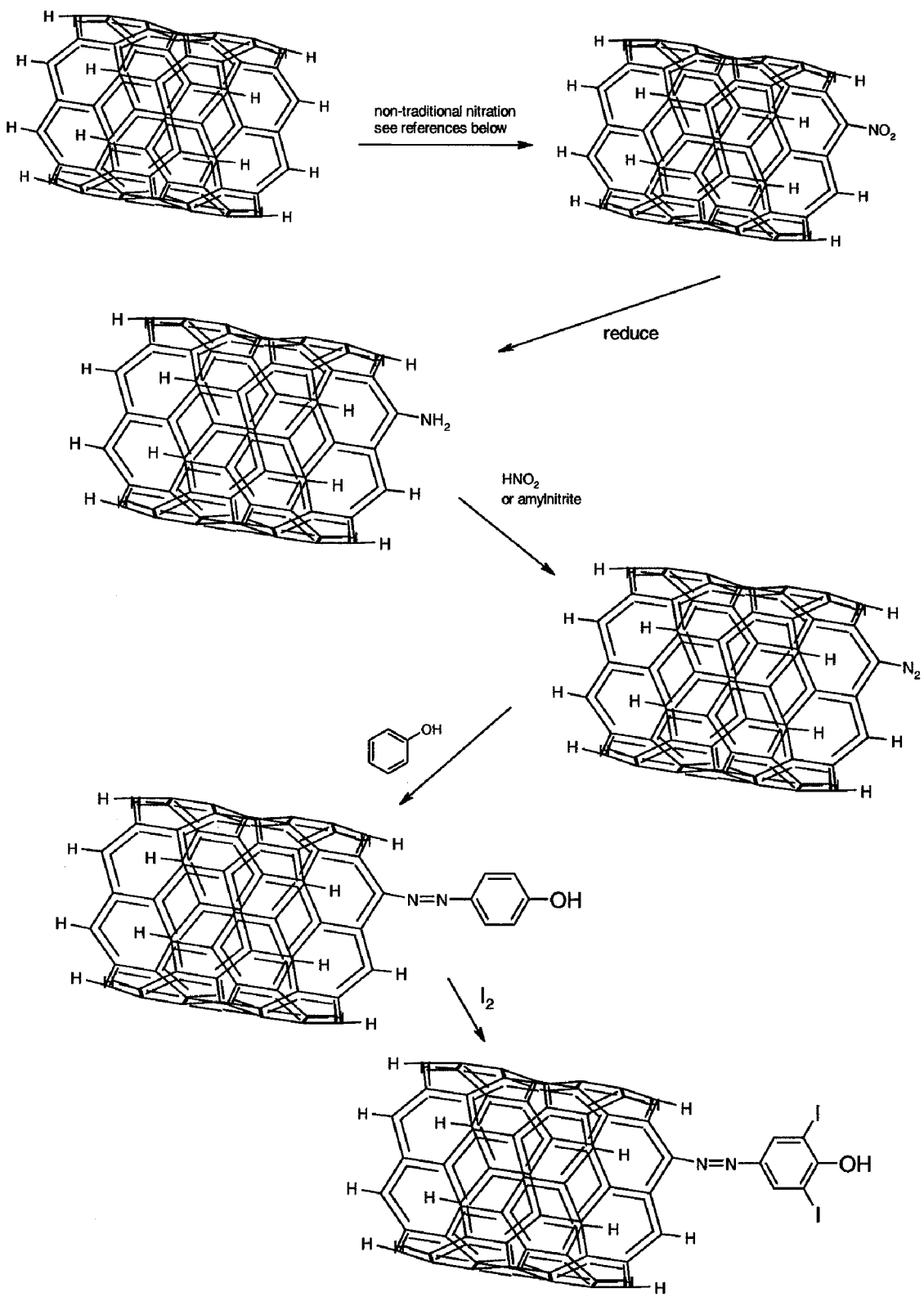
FIG. 2 illustrates, schematically, an embodiment of the present invention, wherein iodine-bearing moieties are covalently attached to carbon nanotubes, and wherein at least some of the iodine emits radiation of a therapeutic kind.

The number of radioactive nuclei delivered in such a manner by each CNT can vary from a single atom to thousands, depending on how much is desired and the manner in which the radioactive nuclei are attached to the CNT. Furthermore, the manner in which the radioisotope atoms are attached to the CNT can be of a covalent and/or physisorptive nature. In some embodiments, this is an intercalation process. Numerous methods exist for attaching such radioactive species to CNTs. Shown in FIG. 2 are some exemplary methods of attaching iodine to CNTs based on a non-traditional nitration of 6 to 7. See Korfmacher et al., J. High Resolut. Chrom. Commun., (1984) 7: 581-583; and Miller et al., J. Org. Chem., (1992) 57: 3746-3748. The reaction scheme ultimately leads to 11 with radioactive iodine attached to the end of the CNT.

In some embodiments, the radioisotope atoms (or molecules) are activated (i.e., generated) before being attached to the CNTs, whereas in other embodiments, they are activated post-attachment. One exemplary method of radioisotope activation comprises the laser-driven photo-transmutation of $^{129}I$ (a long-lived nuclear waste product) to $^{128}I$ by irradiating a gold target with laser pulses from a Nd:glass laser with wavelength $\lambda\sim1$ micron. Relativistic electrons from the ensuing hot plasma are converted to high-energy bremsstrahlung in the target. The gamma radiation from the target induces transmutation of the iodine samples through (y, n) reactions [see Ledingham et al., J. Phys. D: Appl. Phys., (2003) 36: L79-L82, incorporated herein by reference]. Other forms of gamma radiation (e.g., $^{60}Co$) may also be used to carry out such a transmutation. Alternatively, neutron activation may be used.

Because the radioactive atoms (or molecules) are activated before treatment, no subsequent activation is required once the IgG carrier molecules have reached their target tissue, such as discussed above for the BNnt and IgG method described above. In some embodiments, this allows for the targeting of individual molecules that are located outside of tumor sites. For instance, a target molecule located within the bloodstream can be a target for the radioactive CNT-IgG species.

Use of Nanovessels

In other embodiments of the present invention, tumor cloned IgGs are used to carry nanocontainers, probably single walled nanovessels (e.g., single-wall carbon nanotubes), covalently bound to the IgGs, to the tumor sites. Ultrasound waves with a frequency that is absorbed by the nanotubes (~20-40 KHz), are used to explode the carbon nanotubes in the proximity of the tumor. Such use of ultrasound waves to explode carbon nanotubes is analogous to the ultrasound method that is used to destroy kidney stones. Ultrasound is capable of penetrating deep through tissue without tissue damage because the frequency of the waves can be adjusted to be absorbed only by the target, here carbon or other nanostructures. The technique can also be used to deliver effective chemotherapeutic substances, toxic to a tumor, encapsulated inside the nanostructures. Some examples of toxic materials are inorganic substances such as arsenic oxide (AsO), cadmium, cisplatin, etc., as well as organic chemotherapeutic agents such as vinblastine/vincristine, ifosfamide, etoposide, etc. Unfortunately, while these chemotherapeutic agents are very effective at destroying cells through various mechanisms, they do not discriminate between healthy cells and tumor cells. This can result in the severe side effects that are associated with conventional chemotherapy. However, by using the IgGs to deliver drug-filled nanostructures directly to a tumor, then using ultrasonic waves to break open the nanostructures and release the tumor-toxic substances at the site of the tumor, many of the side effects can be reduced or eliminated. In each case, the IgGs are used to carry nanostructures specifically to a tumor, and ultrasonic waves are used to either explode or break open the nanotubes, destroying the tumor.

As discussed above, a practical aspect surrounding certain embodiments of the present invention is the use of covalently-linked IgG targeting. In such case, it is believed that there may be advantages in separating, prior to injection into a patient, the non-linked nanotubes from those that have been successfully linked. This can be accomplished rapidly using separation techniques such as field flow fractionation, size exclusion chromatography, differential centrifugation, etc. To reduce sample volume following separation, liquid-liquid extraction, electrostatic precipitation, centrifugation with decanting, or filtering may be required. It is believed that any non-targeted toxicity from nanoscale particles interacting with normal tissue will be avoided if the only injected nanoparticles are covalently bound to IgGs, which are much larger, protein-scale entities.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Example 1

This Example serves to illustrate, by way of a calculation, the efficiency by which BN nanotubes can deliver radiation to a tumor site in BNCT. A 1 μg amount of BNnt is shown to locally deliver 0.43 microcuries (μc).

$$N = \frac{\phi V \sum_a}{\lambda}(1 - e^{-\lambda t})$$

$$A_0 = N_1\lambda_1 + N_2\lambda_2$$
$$N_1\lambda_1 = \sigma_{a1}N_0\phi$$
$$N_2\lambda_2 = \sigma'_{a2}N_0\phi$$

$$\overline{\sigma}_{a1} = \sigma_{a298}\left(\frac{\sqrt{\pi}}{2}\right)\sqrt{\frac{293}{T}}$$
$$= (\sigma_a^\alpha)(0.868)$$
$$= (3,838b)(0.868)$$
$$= 3,332.5b$$
$$= 3332.5 \times 10^{-24}\ cm^2$$

$$^{19.99\%}_{10}B \Rightarrow \sigma_a^\alpha = 3838b$$

$$_{11}B \xrightarrow{80.0\%} \sigma_a^\alpha = 5\ mb$$

boron atoms in 0.001 grams BN nanotubes    neutrons/s $$A_0 = \frac{(3332.5 \times 10^{-24}\ cm^2)(2.4 \times 10^{16})(1 \times 10^9)}{3.7 \times 10^4\ dps/\mu c}$$

$$t_{1/2} = \frac{0.693}{\lambda} \quad = (2.16\ \mu c)(0.20) \checkmark\ \%\ activated$$
$$= 0.43\ \mu c\ (for\ 0.001\ g\ of\ BN\ nanotubes\ delivered)$$

where:
N is the number of radioactive nuclei activated by the neutron beam.
φ=neutron flux
V=volume of targeted atoms
σ=sum of all nuclei which can be activated
λ=decay constant
T=time of activation Example 2

This Example serves to illustrate the efficiency by which radioactive-laden CNT-IgG species can deliver radiation. In the calculation below, each 1 μg of CNTs administered to a mammalian subject, wherein each CNT carries only 1 $^{128}$I atoms, it is believed at least about 3 curies of radiation is delivered.

$$^{128}_{53}I \rightarrow ^{128}Xe + \beta^{-1} + \alpha$$

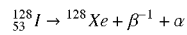

$$N = N_0 e^{-\lambda t}$$

$$A = \lambda N = \lambda N_0 e^{-\lambda t}$$

-continued $$\lambda = \frac{\ln 2}{t_{1/2}} = \frac{0.693}{25 \text{ min}} = 0.027721 \text{ min}^{-1}$$

MW of 100 C atom nanotube with 10 $^{128}$I per nanotube: ≈2600 g/mol

If 0.001 grams of nanotubes are delivered:

$$\frac{0.001 \text{ g}}{2600 \text{ g/mol}} = 3.8 \times 10^{-7} \text{ moles nanotubes}$$

MW of 1000 C atom nanotube with 10 $^{128}$I per nanotube: ≈14,480 g/mol $$\frac{0.001 \text{ g}}{14,480 \text{ g/mol}} = 6.9 \times 10^{-8} \text{ moles nanotubes}$$

$N_0 = (6.91 \times 10^{-8} \text{ moles})(6.02 \times 10^{23}) = 4.157 \times 10^{16}$ I atoms per 0.001 grams of 1000 C atom nanotube or $2.318 \times 10^{17}$ I atoms per 0.001 grams of 100 C atom nanotube $A = \lambda N = (0.0277 \text{ min}^{-1})(4.157 \times 10^{16} \text{ I atoms})(e^{-0.02772})$
$= 1.12 \times 10^{15}$ dpm = 30,270 Curies/mole of 1000 C atom nanotube however, after 1 min→=3 curies per 1 µg of 1 I atom per 1000 C atom nanotube and→=33 curies per 1 µg of 1 I atom per 100 C atom nanotube The novel therapies described herein are generally applicable to all types of cancers. They potentially have the ability, through one treatment, or a series of treatments, to completely cure a person of a particular cancer. Some embodiments of the invention, such as those comprising the radiation-laden nanostructure-IgG species and the diffuse activation of BNnt-IgG species, are even capable of seeking out metastasized cancer cells and destroying them. Embodiments comprising BN nanotube-IgG species provide an excellent means for implementing boron neutron capture therapy—which is currently gaining favor around the globe. BNnt-based therapies have the potential to make BNCT significantly more powerful and specific than it currently is, and allow it to treat much larger tumor masses and organs. In addition, techniques using ultrasound waves to target carbon nanotubes delivered by IgGs specifically to tumor sites, can kill a tumor without the use of nuclear radiation. This latter group of techniques not only provides an alternative way to target and injure or kill cells (fragmenting tubes), but also shows how to empty a tube without having to develop and validate a specific enzyme-activated removable cap. Finally, the present invention provides a way to systematically characterize the specificity of the IgG "tractor" for each patient before beginning the treatment phase through the use of a small amount of radioisotopes attached to an IgG via the mechanisms mentioned. The small amount of radiation delivered by such a tractor can act as a tracer in the body, capable of being viewed using a radioactive scanning technique such as PET.

Use of Encapsulation

Figure 3:
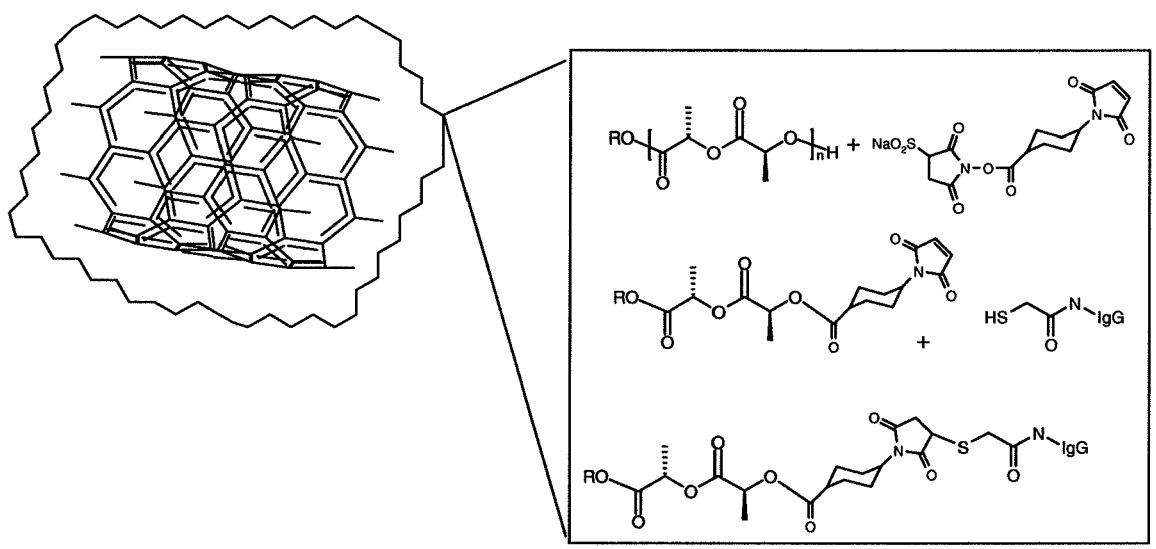
FIG. 3 illustrates, embodiments of the present invention wherein the nanostructures are encapsulated with polylactic acid (an exemplary bio-polymer) and covalently bound to an IgG through the reaction detailed in the box.

In some embodiments of the invention, polymers or bio-polymers can be used to encapsulate the BN, BCN, and CNT nanostructures. For example the bio-polymer polylactic acid can be used to encapsulate the nanostructures—which can be further functionalized and covalently linked to IgG. This can circumvent having to link the IgG to the nanostructures directly. FIG. 3 illustrates of the embodiments described above. The chemistry depicted in FIG. 3 is only an example of linker chemistry for polylactic acid capsule-IgG binding and is not the only type of linker chemistry. For example, polylactic acid of approximately 120,000 $M_w$ mol weight can be obtained in 30 min in solvents such as methylene chloride and ethyl acetate (Macromol. Rapid Commun. 25, 1402, 2004). Polylactic acid possesses a lipophilic character that may enhance its ability to pass through a cell membrane.

Another example of a bio-polymer that could be used to encapsulate the nanostructures is polyaspartic acid. Polyaspartic acid, which contains an amide linkage, a terminal amine, and multiple carboxylic acids for favorable solvent polarity, can also be used to encapsulate nanoparticles. Encapsulating materials such as these bio-polymers reduce potential nanoparticle toxicity and enhance the solubility of the IgG-nanostructure complexes in biological fluids.

Standard microencapsulation methods can be used to achieve encapsulation of the nanostructures by the bio-polymers. Examples of these methods include, but are not limite to, emulsification methods, electrospray techniques, and potentially ultrasonic nebulization. Embodiments of the present invention encompasses the use of any technique that produces a thin coating of the nanostructure, where the coating can be used to improve membrane passage or other physico/chemical characteristics of the nanostructure, to reduce incidental or unintended toxicity of the nanostructure, and/or to facilitate irreversible attachment of the nanostructure to an IgG, antibody, or other cell-targeting species.

Many variations exist for this invention. The chemistry for attachment of BN nanotubes and carbon nanotubes to the IgGs can be optimized for particular therapies. The number of nanotubes that can be covalently bonded to each IgG can be varied. The size of the nanotubes (either BN or carbon) attached to each IgG can be varied. The frequency of the ultrasound waves used to explode or break open nanotubes can be varied to produce a variety of outcomes for a variety of structures.

In addition to the therapeutic methods made possible by the present invention, nanotubes and nanovessels, comprising atoms and/or molecules with suitable nuclei and linked with one or more IgGs, can be used in the diagnostic imaging of tumors.

Recently, Applicants have discovered that cancer cells seem to die in the presence of carbon nanofibers, while non-cancerous cells are unaffected. Thus, the present invention is also directed to methods by which carbon nanofibers linked to IgG molecules are delivered to cancer cells for the purpose of killing them without using any radioisotope, chemical agent, or intentional physical disruption of targeted cells.

Further, any or all of the abovementioned therapies may be employed for a single patient for a given set of circumstances (e.g., combination therapies). These therapies can be performed sequentially or simultaneously. For instance, the BNnt-IgG therapy can be performed first, followed by the radioactive CNT-IgG therapy. In such combination therapies, the IgGs utilized during each can be the same or, alternatively, different IgGs for each therapy. Since the different IgGs can be selected to attach to different portions of the targeted specie, it is believed that there may be some advantage to using different IgGs during combination therapies.

Lastly, any of the methods described herein may be applicable for treating other maladies and should not be construed as being limited to cancer therapies and/or diagnostic techniques. As an example, BNCT has been shown to be applicable for palliative treatment of rheumatoid arthritis (its use being termed radiation synovectomy). See Yanch et al., Med. Phys., (1999) 26: 364-375, incorporated herein by reference.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method for treating cancer, said method comprising:
   a) attaching a first antibody species to nanovessels to form a nanovessel-antibody composite species;
   b) introducing said nanovessel-antibody composite species into a mammal such that said nanovessel-antibody composite species selectively targets at least one type of cancerous cell; and
   c) exploding said nanovessels using at least one frequency of ultrasonic waves;
   wherein said at least one frequency of ultrasonic waves is adjusted to be absorbed by said nanovessels;
   d) attaching a second antibody species to BN nanostructures to form a BN nanostructure-antibody composite species, wherein said first antibody species and said second antibody species are selected from the group consisting of the same antibody species, different antibody species, and combinations thereof;
   e) administering said BN nano structure-antibody composite species to said mammal such that said BN nanostructure-antibody composite species selectively targets at least one tumor within said mammal; and
   f) activating at least some of the boron atoms in said BN nanostructure-antibody composite species.

2. The method of claim 1, wherein said BN nanostructures are encapsulated with a bio-polymer, and wherein said second antibody species is attached to said BN nanostructures through said blo-polymer.

3. The method of claim 1, wherein the step of activating comprises irradiation with transdermal neutrons.

4. A method for treating cancer, said method comprising:
   a) attaching a first antibody species to nanovessels to form a nanovessel-antibody composite species;
   b) introducing said nanovessel-antibody composite species into a mammal such that said nanovessel-antibody composite species selectively targets at least one type of cancerous cell; and
   c) exploding said nanovessels using at least one frequency of ultrasonic waves;
   wherein said at least one frequency of ultrasonic waves is adjusted to be absorbed by said nanovessels;
   d) attaching at least one radioactive isotope to carbon nanotubes to form at least one radioactive-laden carbon nanotube;
   e) attaching a second antibody species to said at least one radioactive-laden carbon nanotube to form a radioactive-laden carbon nanotube-antibody species; and
   f) introducing said radioactive-laden carbon nanotube-antibody species into said mammal such that said radioactive-laden carbon nanotube-antibody species selectively targets at least one tumor with radiation.

5. The method of claim 4, wherein said carbon nanotubes are encapsulated with a bio-polymer, and wherein at least one component selected from the group consisting of said second antibody species and said at least one radioactive isotope is attached to said carbon nanotubes through said bio-polymer.

6. A method for treating cancer, said method comprising:
   a) attaching a first IgG species to at least one BN nanotube to form a BN nanotube-IgG composite species;
   b) administering said BN nanotube-IgG composite species to a mammal such that said BN nanotube-IgG composite species selectively targets at least one tumor within said mammal;
   c) activating at least some of the boron atoms in said BN nanotube-IgG composite species;
   d) attaching at least one radioactive isotope to at least one carbon nanotube to form at least one radioactive-laden carbon nanotube;
   e) attaching a second IgG species to said at least one radioactive-laden carbon nanotube to form a radioactive-laden carbon nanotube-IgG species;
   f) introducing said radioactive-laden carbon nanotube-IgG species into said mammal;
   g) attaching a third IgG species to at least one nanovessel to form a nanovessel-IgG composite species;
   h) introducing said nanovessel-IgG composite species into said mammal such that said nanovessel-IgG composite species selectively targets at least one type of cancerous cell; and
   i) exploding said at least one nanovessel using at least one frequency of ultrasonic waves.

7. The method of claim 6, wherein said first IgG species, said second IgG species, and said third IgG species are selected from the group consisting of the same IgG species, different IgG species, and combinations thereof.

8. The method of claim 6, wherein said at least one BN nanotube is encapsulated with a bio-polymer.

9. The method of claim 8, wherein said first IgG species is attached to said at least one BN nanotube through said bio-polymer.

10. The method of claim 6, wherein said at least one carbon nanotube is encapsulated with a bio-polymer.

11. The method of claim 10, wherein said second IgG species is attached to said at least one carbon nanotube through said bio-polymer.

12. The method of claim 6, wherein said at least one nanovessel is encapsulated with a bio-polymer.

13. The method of claim 12, wherein at least one of said third IgG species is attached to said at least one nanovessel through said bio-polymer.

* * * * *

UNITED STATES PATENT AND TRADEMARK OFFICE
CERTIFICATE OF CORRECTION

| | | |
|---|---|---|
| PATENT NO. | : 7,608,240 B2 | |
| APPLICATION NO. | : 11/005380 | |
| DATED | : October 27, 2009 | |
| INVENTOR(S) | : Buzatu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1542 days.

Signed and Sealed this

Ninth Day of November, 2010

David J. Kappos
*Director of the United States Patent and Trademark Office*